(12) United States Patent
Muller et al.

(10) Patent No.: US 8,906,950 B2
(45) Date of Patent: *Dec. 9, 2014

(54) KETOROLAC TROMETHAMINE COMPOSITIONS FOR TREATING OR PREVENTING OCULAR PAIN

(71) Applicant: Allergan Sales, LLC, Irvine, CA (US)

(72) Inventors: Christopher A. Muller, Foothill Ranch, CA (US); Janet K. Cheetham, Laguna Niguel, CA (US); Teresa H. Kuan, Placentia, CA (US); David F. Power, Trabuco Canyon, CA (US)

(73) Assignee: Allergan Sales, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/830,080

(22) Filed: Mar. 14, 2013

(65) Prior Publication Data

US 2013/0203833 A1 Aug. 8, 2013

Related U.S. Application Data

(63) Continuation of application No. 13/740,426, filed on Jan. 14, 2013, now Pat. No. 8,541,463, which is a continuation of application No. 13/434,956, filed on Mar. 30, 2012, now Pat. No. 8,377,982, which is a continuation of application No. 11/842,915, filed on Oct. 17, 2007, now Pat. No. 8,207,215, which is a continuation of application No. 10/856,192, filed on May 28, 2004, now Pat. No. 8,008,338.

(60) Provisional application No. 60/475,683, filed on Jun. 3, 2003.

(51) Int. Cl.
 *A61K 31/40* (2006.01)
(52) U.S. Cl.
 USPC ............................... 514/413; 514/912
(58) Field of Classification Search
 USPC .................................... 514/413, 912
 See application file for complete search history.

(56) References Cited

U.S. PATENT DOCUMENTS

| | | | | |
|---|---|---|---|---|
| 4,089,969 A | * | 5/1978 | Muchowski et al. | 514/416 |
| 4,454,151 A | * | 6/1984 | Waterbury | 514/413 |
| 5,110,493 A | * | 5/1992 | Cherng-Chyi et al. | 514/413 |
| 5,414,011 A | * | 5/1995 | Fu et al. | 514/413 |
| 5,558,876 A | * | 9/1996 | Desai et al. | 424/427 |
| 5,721,275 A | * | 2/1998 | Bazzano | 514/559 |
| RE41,134 E | | 2/2010 | Bazzano | |

FOREIGN PATENT DOCUMENTS

| | | |
|---|---|---|
| EP | 0306984 | 3/1989 |
| EP | 0390071 | 10/1990 |

OTHER PUBLICATIONS

Acular LS® Prescription Information, 4 pages, Retrieval Date: Jan. 6, 2012, http://www.allergan.com/assets/pdf/acular_is_pi.pdf.
Acular PF, 5 pages, Retrieval Date: Jan. 6, 2012, http://www.drugs.com/pro/acular-pf.html?printable=1.
Acular® Product Label, 5 pages, Retrieval Date: Jan. 6, 2012, http://www.drugs.com/pro/acular.html?printable=1.
Antimicrobial Effectiveness Testing, The United States Pharmacopeia, Jan. 1, 2013, 2002-2004, 26th Edition.
Assouline, Michael et al, A Prospective Randomized Trial of Topical Soluble 0.1% Indomethacin Versus 0.1% Dislofenac Versus Placebo for the Control of Pain Following Excimer Laser Photorefractive Keratectomy, Ophthalmic Surgery Laser, 1998, 365-374, 29(5).
Banker, Gilbert et al, Modern Pharmaceutics, 2002, 450,676, 4th Edition.
Bapatla, Krishna et al, Ophthalmic Ointments and Suspensions, Pharmaceutical Dosage Forms: Diperse Systems, 1989, 461-494, 2.
Boylan, J.C., Liquids, The Theory and Practice of Industrial Pharmacy, 1986, 457-478, 3rd Edition.
Burgalassi, Susi et al, Cytotoxicity of Potential Ocular Permeation Enhancers Evaluated on Rabbit and Human Corneal Epithelial Cell Lines, Toxicol. Lett., 2001, 1-8, 122(1).
Carter, S.J., 29: Ophthalmic Products, Cooper and Gunn's Dispensing for Pharmaceutical Students, 1975, 634-662, 12th Edition.
Chiambaretta, F. et al, Ocular Tolerance of a New Formulation of Nonpreserved Diclofenac, J. Fr. Ophthalmol., 2004, 739-744 (English Abstract), 27(7).
Fielder, Michael, Clinical Implications of Ketorolac for Postoperative Analgesia, Journal of PeriAnesthesia Nursing, Dec. 1997, 426-433, 12(6).
Flach, Allan, Topically Applied Nonsteroidal Anti-inflammatory Drugs and Corneal Problems: an Interim Review and Comment, Ophthalmology, Jul. 2000, 1224-1226, 107(7).
Furrer, Pascal et al, Ocular Tolerance of Absorption Enhancers in Ophthalmic Preparations, Aaps PharmSci, 2002, 1-5, 4(1).
Furrer, Pascal et al, Ocular Tolerance of Preservatives and Alternatives, European Journal of Pharmaceutics and Biopharmaceutics, 2002, 263-280, 53.
Gaynes, Bruce et al, Topical Nonsteroidal Anti-Inflammatory Drugs for Ophthalmic Use: A Safety Review, Drug Safety, 2002, 233-250, 25(4).
Guidera, Ann et al, Keratitis, Ulceration, and Perforation Associated with Topical Nonsteroidal Anti-Inflammatory Drugs, the American Academy of Ophthalmology, 2001, 936-944, 108(5).
Hecht, Gerald, Ophthalmic Preparations, Remington: The Science and Practice of Pharmacy, 2000, 819-835, 20 edition.
Jaanus, Siret et al, Antiinflammatory Drugs, Clinical Ocular Pharmacology, 2001, 265-298.
Koay, Peter, The Emerging Roles of Topical Non-Steroidal Anti-Inflammatory Agents in Ophthalmology, Brit. J. Ophthalmology, 1996, 1117.
Kronemyer, Bob, Acular Reformulated to Reduce Ocular Pain, Burning, Stinging, Ocular Surgery News, Sep. 15, 2003, 48.
Madhu, Cherukury et al, Effect of Benzalkonium Chloride/EDTA on the Ocular Bioavailability of Ketorolac Tromethamine Following Ocular Instillation to Normal and De-epithelialized Corneas of Rabbits, Journal of Pharmaceutical Sciences, Apr. 1996, 415-418, 85(4).
Malhotra, Manjusha et al, Effect of Preservative, Antioxidant and Viscolizing Agents on in Vitro Transcorneal Permeation of Ketorolac Tromethamine, Indian Journal of Experimental Biology, May 2002, 555-559, 40.

(Continued)

*Primary Examiner* — Zohreh Fay
(74) *Attorney, Agent, or Firm* — Mark D. Kafka

(57) ABSTRACT

Compositions comprising ketorolac tromethamine at a therapeutically effective concentration of less than 0.5% are disclosed herein. Methods of treating or preventing ocular pain using said compositions are also disclosed herein.

16 Claims, 5 Drawing Sheets

(56) References Cited

OTHER PUBLICATIONS

Figure 1:
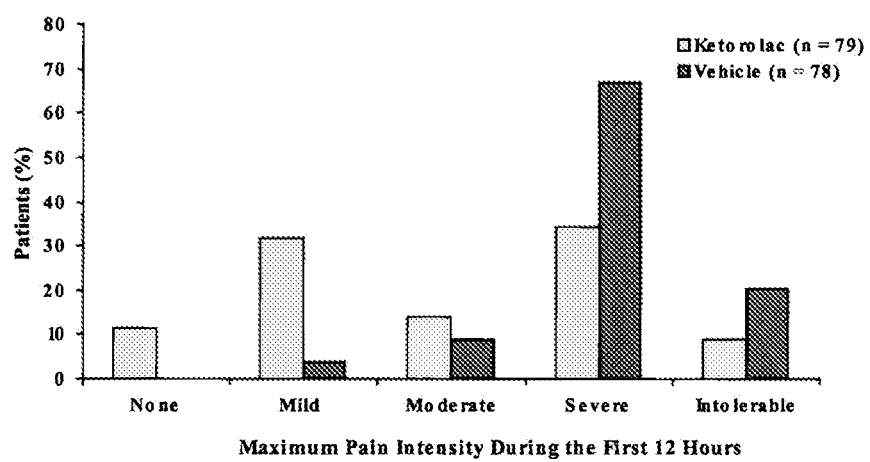

Malhotra, Manjusha et al, In Vivo Ocular Availability of Ketorolac Following Ocular Instillations of Aqueous, Oil, and Ointment Formulations to Normal Corneas of Rabbits: a Technical Note, AAPS PharmSciTech, 2005, E523-E526, 6(3).

Marsh, R.J., The Influence of Non-Ionic Detergents and Other Surfactants on Human Corneal Permeability, Exp. Eye Res., 1971, 43-48, 11.

Maurer, James et al, Ocular Irritation: Microscopic Changes Occurring Over Time in the Rat with Surfactants of Known Irritancy, Toxicologic Pathology, 1998, 217-225, 26(2).

Maurer, James et al, Ocular Irritation: Pathological Changes Occurring in the Rat with Surfactants of Unknown Irritancy, Toxicologic Pathology, 1998, 226-233, 26(2).

Missotten, Luc et al, Topical 0.1% Indomethacin Solution Versus Topical 0.1% Dexamethasone Solution in the Prevention of Inflammation After Cataract Surgery, Ophthalmologica, 2001, 43-50, 215.

Ophthalmic nonsteroidal Anti-Inflammatory Drugs (NSAIDs) Review, Sep. 2008, 8 pages, Provider Synergies.

Ophthalmic Ointments, 26 U.S. Pharmacopeia, 2003, 2183-2184.

Price, F. et al, Safety and Efficacy of Reformulated Ketorolac Tromethamine 0.4% Ophthalmic Solution in Post-Photorefractive Keratectomy Patients, Association for Research and Vision in Ophthalmology, Presented May 6, 2003, Poster 2611, 8:30am.

Rooks, W.H., The Analgesic and Anti-Inflammatory profile of Ketorolac and Its Tromethamine Salt, Drugs Exptl. Clin. Res., 1985, 479-492, XI(8).

Rooks, W.H., The Pharmacologic Activity of Ketorolac Tromethamine, Pharmacotherapy, 1990, 30S-32S, 10(Supp 6).

Rowland, Malcolm et al, Clinical Pharmacokinetics: Concepts and Applications, 1995, 61, 3.

Ruggiero, Ronald, Prescription Contraceptives: Countering the Risks, American Pharmacy, Sep. 1985, 32-37, NS25(9).

Sandoval, Helga et al, Evaluation of 0.4% Ketorolac Tromethamine Ophthalmic Solution Versus 0.5% Ketorolac Tromethamine Ophthalmic Solution After Phacoemulsification and Intraocular Lens Implantation, Journal of Ocular Pharmacology and Therapeutics, 2006, 251-257, 22(4).

Sasaki, Hitoshi et al, Ophthalmic Preservatives As Absorption Promoters for Ocular Drug Delivery, J. Pharm. Pharmacol., 1995, 703-707, 47, US.

Sheppard, John, Using NSAIDs to Full Potential: Expert Guidance on Maximizing Utility, Ophthalmology MGMT, 1112001, 3 pages.

Solomon, Kerry et al, Comparison of Ketorolac Tromethamine 0.5% and Rimexolone 1% to Control Inflammation After Cataract Extraction, J Cataract Refract Surg, 2001, 1232-1237, 27.

Stahl, Heinrich et al, Handbook of Pharmaceutical Salts: Properties, Selection, and Use, 2002, 324-325, International Union of Pure and Applied Chemistry.

Teal, Patricia et al, Corneal Subepithelial Infiltrates Following Excimer Laser Photorefractive Keratectomy, J Cataract Refract Surg, 1995, 516-518, 21(5).

The Cosmetic Ingredient Review Expert Panel, Safety Assessment of Salicyclic Acid, Butyloctyl Salicylate, Calcium Salicylate, C12-15 Alky Salicylate, Capryloyl Salicylic Acid, Hexyldodecyl Salicylate, Isocetyl Salicylate, Isodecyl Salicylate, Magnesium Salicylate, Mea-Salicylate, Ethylhexyl Salicylate, Potassium Salicylate, Methyl Salicylate, Myristy Salicylate, Sodium Salicylate, Tea- Salicylate, and Tridecyl Salicylate, 22 (Suppl. 3) Intl J. Toxicology 1 (2003).

Thomas Abrams, Warning Letter, May 25, 2007, 7 pages, Food and Drug Administration, Rockville, MD.

Tutton, Miles et al, Efficacy and Safety of Topical Diclofenac in Reducing Ocular Pain After Excimer Photorefractive Keratectomy, J Cataract Refract Surg, 0611996, 536, 22(5).

Waterbury, David et al, Comparison of Ketorolac Tromethamine, Diclofenac Sodium, and Loteprednol Etabonate in an Animal Model of Ocular Inflammation, Journal of Ocular Pharmacology and Therapeutics, 2006, 155-159, 22(3).

Waterbury, David et al, Efficacy of Low Concentrations of Ketorolac Tromethamine in Animal Models of Ocular Inflammation, Journal of Ocular Pharmacology and Therapeutics, 2004, 345-352, 20(4).

Whittpenn, John, Acular LS: Reduced Discomfort without Loss of Efficiency, Ophthalmology Management, Aug. 2003, 12-15, 7(Suppl 8).

* cited by examiner

Overall *P* < .001 for the distribution of scores for ketorolac 0.4% vs vehicle

Overall $P < .001$ for 0.4% ketorolac tromethamine vs vehicle (Kaplan-Meier analysis)

Arrows indicate median time to first no pain. No pain recorded as the maximum pain intensity score during that period.

Overall $P<.001$ vs vehicle

Pain relief scored on a 5-point scale, where 0 = no pain relief through 4 = complete pain relief.

*$P \leq .006$ vs vehicle-treated patients, **$P < .001$ vs vehicle-treated patients Overall $P = .016$ for ketorolac 0.4% vs vehicle, (Kaplan-Meir analysis)

KETOROLAC TROMETHAMINE COMPOSITIONS FOR TREATING OR PREVENTING OCULAR PAIN

CROSS REFERENCE TO RELATED APPLICATIONS

This application is a continuation application of U.S. patent application Ser. No. 13/740,426, filed Jan. 14, 2013, which is a continuation of U.S. patent application Ser. No. 13/434,956, filed Mar. 30, 2012, which is a continuation of U.S. patent application Ser. No. 11/842,915, filed Oct. 17, 2007, now U.S. Pat. No. 8,207,215, issued Jun. 26, 2012, which is a continuation application of U.S. patent application Ser. No. 10/856,192, filed May 28, 2004, now U.S. Pat. No. 8,008,338, issued Aug. 30, 2011, which claims priority to U.S. Provisional Patent Application Ser. No. 60/475,683, filed Jun. 3, 2003, all of which are hereby incorporated herein by reference.

BACKGROUND OF THE INVENTION

1. Field of the Invention

This invention relates to pharmaceutical compositions. More particularly, this invention relates to topical ophthalmic compositions comprising 5-benzoyl-2,3-dihydro-1H-pyrrolizine-1-carboxylic acid, otherwise known as ketorolac.

2. Description of the Related Art

Topical nonsteroidal anti-inflammatory drugs (NSAIDs) are used to control pain and postoperative inflammation. All drugs are associated with some adverse effects. With the use of NSAIDS in topical ophthalmic treatment of patients, surface toxicity has been a concern, and incidents of keratitis, corneal subepithelial infiltrates, ulceration, and corneal melts have been reported (Guidera et al, *Ophthalmology,* 2001, 108 (5), pp. 936-944; Solomon et al, *J Cataract Refract Surg,* 2001, 27 (8), pp. 1232-1237; Teal et al, *J Cataract Refract Surg,* 1995, 21(5), pp. 516-518). Further, patients often report burning or stinging on instillation (Jaanus et al, Antiinflammatory Drugs. Clinical Ocular Pharmacology, Bartlet, J. D. and Jaanus, S. D., Ed., Boston: Heineman, 2001, pp. 265-298). The burning or stinging could be related to the concentration of the active component of the formulation.

Ketorolac tromethamine 0.5% (w/v) ophthalmic solution, available from Allergan, Inc., under the tradename ACULAR®, is a safe and effective NSAID with proven analgesic and anti-inflammatory activity. The most common adverse event associated with the use of the 0.5% ketorolac formulation is ocular irritation, primarily burning, and stinging on instillation. Eliminating or reducing ocular irritation has the potential for improving tolerability, compliance, and effectiveness of treatment.

BRIEF SUMMARY OF THE INVENTION

We have surprisingly discovered that reducing the concentration of ketorolac tromethamine reduces the occurrence of adverse events while maintaining clinical efficacy. Additionally, we have also discovered that the reduced concentration of ketorolac tromethamine offers surprising benefits in terms of formulation in that significantly less preservative, chelating agent, and surfactant are required for effective formulation.

Compositions comprising ketorolac tromethamine at a therapeutically effective concentration of less than 0.5% are disclosed herein. This invention relates to an aqueous topical ophthalmic composition comprising from 0.35% to 0.45% ketorolac tromethamine. Another aspect of this invention relates to a method of treating or preventing ocular pain in a person comprising topically administering to said patient a sterile composition comprising from 0.35% to 0.45% ketorolac tromethamine.

While not intending to limit the scope of this invention in any way, of particular interest in relationship to this invention is the use of aqueous topical ophthalmic compositions of 0.4% (w/v) ketorolac tromethamine for the treatment of ocular pain, especially for the treatment of ocular pain in postoperative photorefractive keratectomy (PRK) surgery patients. It is surprising that the 20% lower concentration of ketorolac as compared to the above ACULAR® product would reduce the incidence of adverse events and enhance comfort while maintaining clinical efficacy.

BRIEF DESCRIPTION OF THE DRAWING FIGURES

FIG. 1: Effect Of Ketorolac 0.4% On Pain Intensity During First 12 Hours Post-Postoperative Photorefractive Keratectomy (PRK) Surgery.

Figure 2:
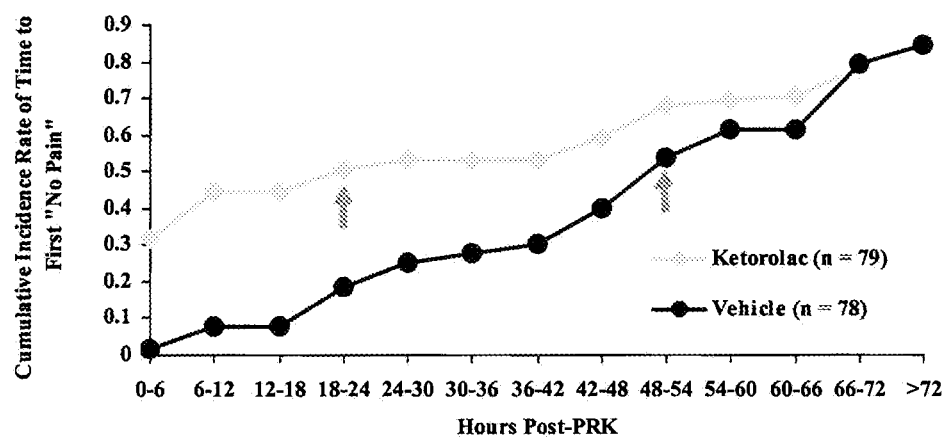

FIG. 2: Time Course for First Achieving "No Pain" With Ketorolac 0.4% vs Vehicle.

Figure 3:
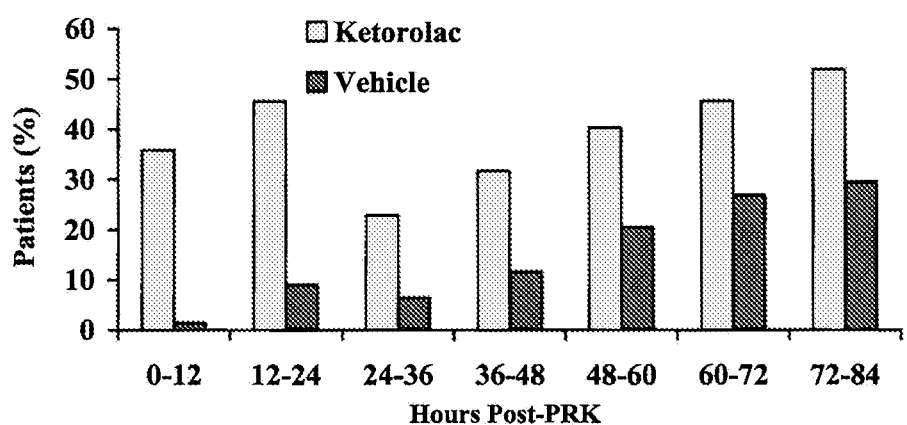

FIG. 3: Percentages of Ketorolac 0.4%- and Vehicle-Treated Patients Experiencing Complete or Great Pain Relief Post-PRK.

Figure 4:
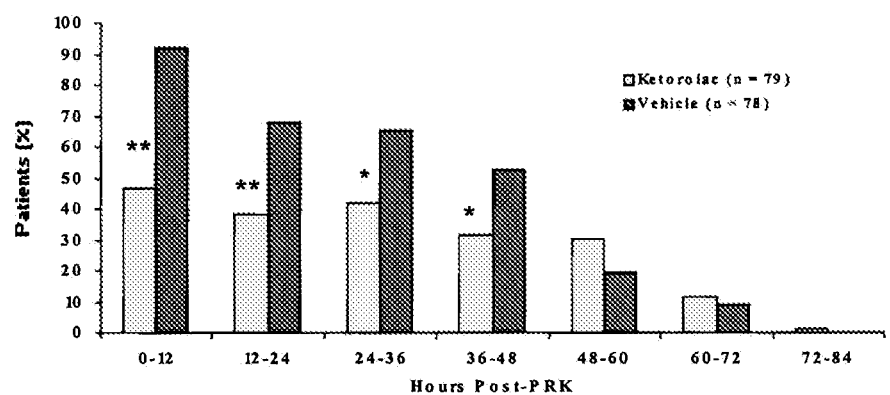

FIG. 4: Percentages of Ketorolac 0.4%- and Vehicle-Treated Patients Requiring Escape Medication.

Figure 5:
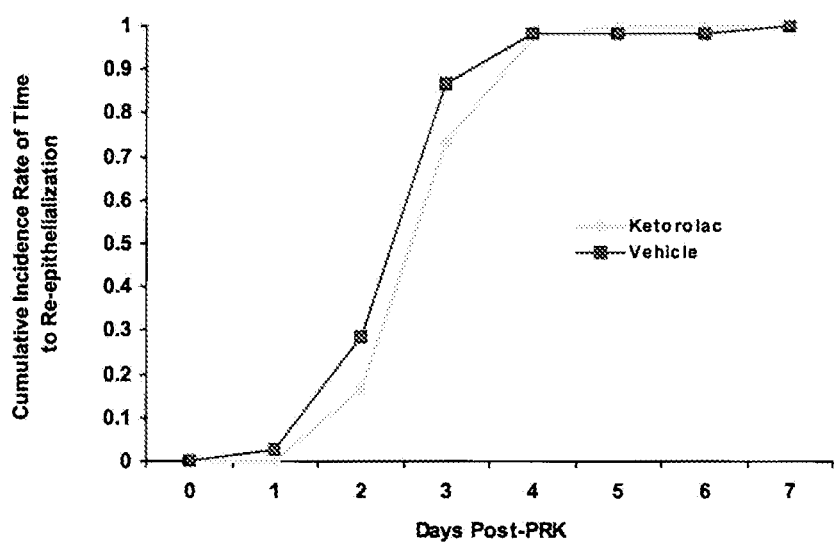

FIG. 5: Rate of Re-epithelialization.

DETAILED DESCRIPTION OF THE INVENTION

All of the aqueous topical ophthalmic compositions of this invention are contemplated for use in treating or preventing ocular pain. Preferably, all of the compositions of this invention are contemplated for use when said ocular pain is a result of photorefractive keratectomy surgery (PRK).

On important aspect of this invention is that these compositions have a concentration of ketorolac tromethamine which is optimized to reduce side effects and improve ease of formulation, while maintaining clinical efficacy in treating ocular pain. As such, the concentration of ketorolac tromethamine in compositions related to this invention should be from 0.35% to 0.45%. Preferably the concentration of ketorolac tromethamine in the aqueous topical ophthalmic composition of this invention is 0.4% ketorolac tromethamine.

The fact that the concentration of ketorolac tromethamine in compositions related to this invention is optimized for ease of formulation is underscored by the surprising observation that compositions of the present invention can be prepared with significantly lower concentrations of preservative, surfactant, and chelating agent than is possible with compositions containing slightly higher concentrations of ketorolac tromethamine.

The term preservative has the meaning commonly understood in the ophthalmic art. Preservatives are used to prevent bacterial contamination in multiple-use ophthalmic preparations, and, while not intending to be limiting, examples include benzalkonium chloride, stabilized oxychloro complexes (otherwise known as PURITE®), phenylmercuric acetate, chlorobutanol, benzyl alcohol, parabens, and thimerosal. Preferably, the preservative is benzalkonium chloride.

The term surfactant used in this invention has the meaning commonly understood in the art. Surfactants are used to help solubilize the therapeutically active agent or other insoluble components of the composition. Anionic, cationic, amphoteric, zwitterionic, and nonionic surfactants may all be used in this invention. Preferably, a nonionic surfactant is used in this invention. While not intending to limit the scope of the invention, some examples of useful nonionic surfactants are polysorbates, poloxamers, alcohol ethoxylates, ethylene glycol-propylene glycol block copolymers, fatty acid amides, and alkylphenol ethoxylates, and phospholipids. Most preferably, the surfactant is an octylphenol ethoxylate with an average of 40 ethoxylate groups. This type of surfactant, also known as octoxynol-40 or IGEPAL® CA-897, can be purchased under the IGEPAL® CA-897 tradename from RhOne-Poulenc.

The term chelating agent refers to a compound that is capable of complexing a metal, as understood by those of ordinary skill in the chemical art. Chelating agents are used in ophthalmic compositions to enhance preservative effectiveness. While not intending to be limiting, some useful chelating agents for the purposes of this invention are edetate salts like edetate disodium, edetate calcium disodium, edetate sodium, edetate trisodium, and edetate dipotassium. In the preferred embodiment of this invention edetate disodium is used as the chelating agent.

In addition to surfactants, preservatives, and chelating agents, tonicity agents and other excipients are often used in ophthalmic compositions. Tonicity agents are often used in ophthalmic compositions to adjust the concentration of dissolved material to the desired isotonic range. Tonicity agents are known to those skilled in the ophthalmic art, and, while not intending to be limiting, some examples include glycerin, mannitol, sorbitol, sodium chloride, and other electrolytes. Preferably, the tonicity agent is sodium chloride.

One preferred embodiment of this invention relates to an aqueous topical ophthalmic composition comprising 0.4% ketorolac tromethamine, from 0.001% to 0.05% edetate disodium, from 0.004% to 0.007% benzalkonium chloride, and from 0.001% to 0.005% Octoxynol-40.

Another preferred embodiment of this invention relates to an aqueous topical ophthalmic composition comprising 0.4% ketorolac tromethamine, 0.006% benzalkonium chloride, 0.015% edetate disodium, 0.003% Octoxynol-40, 0.79% sodium chloride, and an effective amount of sodium hydroxide or hydrochloric acid to adjust the pH to from 7.2 to 7.6.

Another preferred embodiment of this invention relates to an aqueous topical ophthalmic composition consisting essentially of 0.4% ketorolac tromethamine, 0.006% benzalkonium chloride, 0.015% edetate disodium, 0.003% Octoxynol-40, 0.79% sodium chloride, and an effective amount of sodium hydroxide or hydrochloric acid to adjust the pH to from 7.2 to 7.6.

The most preferred embodiment of this invention relates to an aqueous topical ophthalmic composition consisting of 0.4% ketorolac tromethamine, 0.006% benzalkonium chloride, 0.015% edetate disodium, 0.003% Octoxynol-40, 0.79% sodium chloride, and an effective amount of sodium hydroxide and/or hydrochloric acid to adjust the pH to from 7.2 to 7.6.

EXAMPLE 1

Unless otherwise specified, all steps in this procedure were carried out at room temperature. The following procedure was followed in accordance with the amounts listed in Table 1 below. Purified water at 90% of batch size was charged into the main batch vessel. Mixing was initiated to produce a vortex sufficient to disperse and/or dissolve all product ingredients without excessive aeration or foam formation. The following components were added directly into the vortex in order, allowing each to dissolve before adding the next: sodium chloride, edetate disodium, octoxynol-40 (as a 70% stock solution) and benzalkonium chloride (as a 10% stock solution). The amount of benzalkonium chloride added took into account the assay of the stock solution used. The solution was mixed for no longer than 15 minutes. A specified amount of 1N sodium hydroxide, 1.85 ml per liter of final bulk product, was then added. The pH was checked and if needed was adjusted to 10.7-11.0 with 1N sodium hydroxide or 1N hydrochloric acid. Ketorolac tromethamine was then added based on "as is" assay and mixed until completely dissolved based on visual inspection. When dissolved, the solution pH was again checked and if needed adjusted to pH 7.3-7.5 (final target pH is 7.4) with 1N sodium hydroxide or 1N hydrochloric acid. Purified water was then added to bring the bulk solution to final volume and allowed to mix for at least 15 minutes to ensure uniformity. The solution was then sterile filtered for use.

TABLE 1

| 0.4% Ketorolac Tromethamine Ophthalmic Solution | |
|---|---|
| Ketorolac Tromethamine | 0.4% |
| Edetate Disodium | 0.015% |
| NaCl | 0.79% |
| Benzalkonium Chloride | 0.006% |
| Octoxynol-40 | 0.003% |
| Ph | 7.4 |

EXAMPLE 2

Table 2 contains the composition of an ophthalmic solution containing 0.5% ketorolac tromethamine which is clinically effective for treating ocular pain following photorefractive keratectomy surgery. The composition was prepared by the same procedure as Example 1. This composition was optimized to minimize the amounts of chelating agent, preservative, and surfactant required, since they are irritating to the eye. Comparison of the 0.5% solution of Table 2 to the 0.4% solution of Table 1 reveals that, surprisingly, the reduction of the amount of chelating agent, preservative, and surfactant required for the 0.4% ketorolac tromethamine is significantly greater than 20%, which corresponds to the reduction in the therapeutic agent.

TABLE 2

| 0.5% Ketorolac Tromethamine Ophthalmic Solution | |
|---|---|
| Ketorolac Tromethamine | 0.5% |
| Edetate Disodium | 0.10% |
| NaCl | 0.79% |
| Benzalkonium Chloride | 0.010% |
| Octoxynol-40 | 0.007% |
| pH | 7.4 |

EXAMPLE 3

A multicenter, randomized, double-masked, vehicle-controlled, parallel-group study was carried out using the 0.4% ketorolac tromethamine formulation of Example 1. The study subjects consisted of 157 patients (78-79/group) undergoing unilateral PRK surgery. The key inclusion criteria for the study were that each subject a) was a candidate for unilateral photorefractive keratectomy surgery (PRK) within 7 days after the initial visit, b) had best-corrected ETDRS visual acuity of 20/100 or better, and c) was capable of wearing a soft bandage contact lens. Key exclusion criteria were a history of refractive ocular surgery and sensitivity to study medication or its vehicle, TYLENOL® #3, or OCUFLOX®. The patient demographics are shown in Table 3. A total of 157 patients were enrolled with an age range of 20-66 years. There were no significant demographic differences between treatment groups.

TABLE 3

Patient Demographics

|  | n | % |
|---|---|---|
| Gender |  |  |
| Female | 91 | 58 |
| Male | 66 | 42 |
| Age, mean ± SD | 39 ± 10 |  |
| Race |  |  |
| Caucasian | 148 | 94 |
| Black | 5 | 3 |
| Hispanic | 2 | 1 |
| Asian | 1 | 1 |
| Other | 1 | 1 |

Each subject received OCUFLOX® 5 min prior to study medication. The study subjects then received ketorolac tromethamine 0.4% ophthalmic solution or vehicle, 1 drop QID for up to 4 days, and the control subjects received the vehicle (i.e. the composition of Table 1 without the ketorolac tromethamine). The all subjects were then instructed to take TYLENOL® #3 as needed for intolerable pain (escape medication). Patients used electronic diaries with date and time stamp to record the ocular pain they experienced as one of the following: no pain, mild, moderate, severe, intolerable.

FIG. 1 shows that the pain intensity was significantly less for the subjects who received ketorolac tromethamine 0.4% (P<0.001) during the first 12 hours post-PRK compared to those who received the vehicle only. In particular, during the first 12 hours post-PRK, the group that received 0.4% ketorolac tromethamine had fewer patients with severe or intolerable pain (43.0%, 34/79) compared with the vehicle group (87.2%, 68/78, P≤0.001). In particular, the median pain intensity reported by the group which received 0.4% ketorolac tromethamine was 1 grade less than with the group which received the vehicle only (moderate vs severe on a 5-point scale of 0=no pain to 4=intolerable pain). This 1-grade difference was considered clinically significant. Additionally, pain intensity was also significantly less for the group which received ketorolac tromethamine compared with the group which received the vehicle only at 12-48 hours post-PRK (P≤0.001, data not shown).

FIG. 2 shows that the onset of pain relief was faster with the group that received 0.4% ketorolac tromethamine compared to the group that received the vehicle only (P<0.001). The median time to first report of no pain was 18-24 hours in the 0.4% ketorolac tromethamine group compared with 48-54 hours for the group which received vehicle only (P<0.001). Furthermore, the initial experience of no pain during the first 12 hours post-PRK was reported by 44.3% (35/79) of patients in the ketorolac tromethamine group compared with 7.8% (6/78) of patients in the vehicle group.

FIG. 3 shows that significantly more of the patients who received 0.4% ketorolac tromethamine reported complete or pain relief than vehicle-treated patients throughout the study up to 84 hours.

In addition to experiencing greater and significantly faster pain relief overall than the vehicle group, the patients who received ketorolac tromethamine also had less incidents of severe pain, as demonstrated by the significantly lower number of ketorolac tromethamine patients who used the escape vehicle. FIG. 4 shows that during the first 12-hours post-PRK, the escape medication was taken by only 46.8% (37/79) of the ketorolac tromethamine patients compared to 92.3% (72/78; P<0.001) of the vehicle patients. Additionally the 0.4% ketorolac tromethamine-treated patients used significantly less escape medication 12-48 hours post-PRK compared with vehicle-treated patients (P≤0.006).

The rate of corneal re-epithelialization was also studied for both groups, as depicted in FIG. 5. Although corneal re-epithelialization occurred more quickly in the vehicle group than in the ketorolac group (P=0.016), the difference was probably not clinically significant. The median time to re-epithelialization was between days 2 and 3 following PRK surgery for both treatment groups.

TABLE 4

Adverse Events (Treatment-Related and Unrelated)

|  | Ketorolac 0.4% Frequency (%) n = 79 | Vehicle Frequency (%) n = 78 |
|---|---|---|
| Eye Pain | 3 (3.8) | 4 (5.1) |
| Headache | 1 (1.3) | 2 (2.6) |
| Corneal Infiltrates | 1 (1.3) | 1 (1.3) |
| Eye Edema | 1 (1.3) | 0 (0.0) |
| Conjunctival Hyperemia | 1 (1.3) | 0 (0.0) |
| Cornea | 0 (0.0) | 1 (1.3) |
| Nausea | 0 (0.0) | 3 (3.8) |
| Nausea/Vomiting | 0 (0.0) | 2 (2.6) |
| Vomiting | 0 (0.0) | 1 (1.3) |
| Rhinitis | 0 (0.0) | 1 (1.3) |

Table 4 shows that adverse events were minor and infrequent for the group that received ketorolac tromethamine. Ocular irritation was not reported, and the ketorolac tromethamine group actually had less adverse events than the vehicle group. At least 1 adverse event was reported for only 6.3% of 0.4% ketorolac tromethamine-treated patients (5/79) compared to 15.4% of vehicle-treated patients (12/78). Furthermore, only 1.3% of 0.4% ketorolac tromethamine-treated patients (1/79) were discontinued from the study due to adverse events compared to 7.7% of vehicle-treated patients (6/78). Changes in visual acuity and biomicroscopic findings in the subjects were as expected post-PRK.

In summary, the 0.4% ketorolac formulation is clinically effective in treating post PRK ocular pain. In comparison with vehicle-treated patients, the 0.4 ketorolac tromethamine-treated patients experienced significantly greater and faster pain relief (P<0.001), and used significantly less escape medication compared to vehicle-treated patients (P≤0.006). Additionally, the 0.4% ketorolac tromethamine formulation has an excellent tolerability profile. Adverse events were minor and infrequent.

EXAMPLE 4

A comfort study was carried out to compare the ocular comfort of the ketorolac tromethamine solution 0.4% with that of a composition containing the composition of Table 5 in healthy volunteers. The composition is the same as that in Table 5 except that no preservative was used, as is a single use formulation.

TABLE 5

0.5% Non-Preserved Ketorolac Tromethamine Ophthalmic Solution

| | |
|---|---|
| Ketorolac Tromethamine | 0.5% |
| Edetate Disodium | 0.10% |
| NaCl | 0.79% |
| Octoxynol-40 | 0.007% |
| pH | 7.4 |

A single center, randomized, investigator-masked, paired-comparison clinical trial was carried out. Forty-five subjects were randomized to receive a single drop of the composition of Table 1 (Formula 1) in one eye and the composition of Table 5 (Formula 2) in the contralateral eye at two evaluations on a single day. Before and after receiving their first set of drops, subjects were asked to rate their ocular discomfort on a scale of 0 to 4, where 0=no discomfort and 4=a definite continuous burning/stinging that last more than 30 seconds. The procedure was repeated 5 minutes after the first set of drops were instilled.

The mean subject discomfort score prior to each drop instillation was 0. Both Formula 1 and Formula 2 were reported to be comfortable, with a mean discomfort score of 0.93 in the Formula 1 group and 0.96 in the Formula 2 group after the first drop instillation (P=0.881). After the second drop instillation, subjects reported that Formula 1 was more comfortable than Formula 2. The mean score was 0.53 in the Formula 1 group, compared with a mean score of 0.87 in the Formula 2 group (P=0.017).

Formula 1 is at least as comfortable upon instillation as Formula 2. In a multi-use formulation such as that of Table 2, it is expected that a 0.4% ketorolac tromethamine solution prepared as disclosed herein will be significantly more comfortable than a 0.5% ketorolac tromethamine solution, while the clinical efficacy of the two compositions are essentially the same.

What is claimed is:

1. A method for treating ocular pain and burning by topical administration no more than four times daily of an aqueous composition comprising 0.4% w/v ketorolac tromethamine.

2. A method for treating ocular pain and burning by topical administration no more than four times daily of an aqueous topical ophthalmic composition comprising 0.4% w/v ketorolac tromethamine, from about 0.001% w/v to about 0.05% w/v edetate disodium, from about 0.004% w/v to about 0.007% w/v benzalkonium chloride, and from about 0.001% w/v to about 0.005% w/v Octoxynol-40, and an effective amount of sodium hydroxide and/or hydrochloric acid to adjust the pH from about 7.2 to about 7.6.

3. A method for treating ocular pain and burning by topical administration no more than four times daily of an aqueous composition comprising 0.4% w/v ketorolac tromethamine, about 0.015% w/v edetate disodium, about 0.006% w/v benzalkonium chloride, about 0.003% w/v Octoxynol-40, about 0.79% w/v sodium chloride, and an effective amount of sodium hydroxide and/or hydrochloric acid to adjust the pH to from about 7.2 to about 7.6.

4. A method for treating ocular pain and burning by topical administration no more than four times daily of an aqueous composition comprising 0.4% w/v ketorolac tromethamine as its sole active ingredient, wherein said method is substantially as effective as topical administration of a second composition comprising 0.5% w/v ketorolac tromethamine as its sole active ingredient at the same dosing frequency.

5. The method of claim 4, wherein said method also provides reduced ocular side effects as compared to topical administration of said second composition comprising 0.5% w/v ketorolac tromethamine as its sole active ingredient at the same dosing frequency.

6. The method of claim 1, wherein the ocular pain and burning is caused by corneal refractive surgery, cataract surgery, or allergic conjunctivitis.

7. The method of claim 2, wherein the ocular pain and burning is caused by corneal refractive surgery, cataract surgery, or allergic conjunctivitis.

8. The method of claim 3, wherein the ocular pain and burning is caused by corneal refractive surgery, cataract surgery, or allergic conjunctivitis.

9. The method of claim 4, wherein the ocular pain and burning is caused by corneal refractive surgery, cataract surgery, or allergic conjunctivitis.

10. The method of claim 5, wherein the reduction in ocular side effects includes at least one side effect selected from the group consisting of ocular discomfort, ocular irritation, ocular stinging, ocular burning, and foreign body sensation.

11. The method of claim 2, wherein said method is substantially as effective as topical administration of a second composition comprising 0.5% w/v ketorolac tromethamine as its sole active ingredient at the same dosing frequency.

12. The method of claim 3, wherein said method is substantially as effective as topical administration of a second composition comprising 0.5% w/v ketorolac tromethamine as its sole active ingredient at the same dosing frequency.

13. The method of claim 11, wherein said method also provides reduced ocular side effects as compared to topical administration of said second composition comprising 0.5% w/v ketorolac tromethamine as its sole active ingredient at the same dosing frequency.

14. The method of claim 12, wherein said method also provides reduced ocular side effects as compared to topical administration of said second composition comprising 0.5% w/v ketorolac tromethamine as its sole active ingredient at the same dosing frequency.

15. The method of claim 13, wherein the reduction in ocular side effects includes at least one side effect selected from the group consisting of ocular discomfort, ocular irritation, ocular stinging, ocular burning, and foreign body sensation.

16. The method of claim 14, wherein the reduction in ocular side effects includes at least one side effect selected from the group consisting of ocular discomfort, ocular irritation, ocular stinging, ocular burning, and foreign body sensation.

* * * * *